United States Patent [19]

Uzzell

[11] Patent Number: 5,042,294
[45] Date of Patent: Aug. 27, 1991

[54] MOISTURE DETECTION PROBE

[76] Inventor: Ken Uzzell, 68 Clarke Street, Narrabeen, Sydney NSW 2101, Australia

[21] Appl. No.: 377,421

[22] Filed: Jul. 10, 1989

[30] Foreign Application Priority Data

Jul. 11, 1988 [AU] Australia ................... PI9241

[51] Int. Cl.$^5$ ............... G01N 25/18; G01N 25/56
[52] U.S. Cl. ................................... 73/75; 374/45
[58] Field of Search ............ 73/75, 73, 77, 29.01, 73/29.02, 29.03, 29.04, 29.05, 335, 336, 336.5, 337, 337.5, 338, 338.3, 338.6, 1 R, 1 G; 374/43, 44, 45, 1-3

[56] References Cited

U.S. PATENT DOCUMENTS

| | | | |
|---|---|---|---|
| 3,832,882 | 9/1974 | Schoen, Jr. | 73/336 X |
| 4,080,821 | 3/1978 | Johnston | 374/44 X |
| 4,197,866 | 4/1980 | Neal | 73/75 X |
| 4,532,797 | 8/1985 | Yang | 73/75 |
| 4,717,811 | 1/1988 | Fujii | 73/75 X |
| 4,774,831 | 10/1988 | Nordin | 73/75 |
| 4,845,978 | 7/1989 | Whitford | 73/75 X |

Primary Examiner—Tom Noland
Attorney, Agent, or Firm—Amster, Rothstein & Ebenstein

[57] ABSTRACT

A probe assembly for the measurement of moisture within a medium by indirect contact with the medium. The probe comprises an apparatus at the leading end of the probe to enable measurement of the moisture level within the medium. The apparatus comprises a thermal conductor linked to a heating source, a temperature sensor for enabling measurement of the heat dissipation rate in the thermal conductor upon isolation of the heating source and a heater for delivering energy from a power source to heat the thermal conductor via the heating source. The probe is surrounded by a controlled environment eliminating the need for pre-calibration of the probe. When the probe is inserted in the medium and the heater is isolated from the power source the heat dissipation rate is measurable and commensurate with the level of moisture in the medium.

22 Claims, 11 Drawing Sheets

MOISTURE DETECTION PROBE

BACKGROUND OF THE INVENTION

The present invention relates to an improved moisture detection probe and in particular to a moisture detection probe which utilises a temperature sensor for detection of moisture present in a medium.

The present invention also provides a moisture sensing probe which provides accurate recordal of moisture content in a medium such as soil by measurement of heat loss in a conductor by a temperature sensor contained in, on or near the conductor preferably located at the extremity of the probe. Unlike the prior art moisture detection probes, the present invention is unaffected by those parameters in soils which have previously created inaccuracies when soil moisture is measured by the prior art probes.

The temperature sensor at the extremity of the probe is less sensitive to changes in parameters in the soil environment and in relation to some parameters such as soil pH the performance of the temperature sensor in as much as its ability to generate accurate results is concerned is unaffected.

Although it is feasible for the present invention to be utilised in measuring moisture contents in a number of mediums the present description will be confined to measurement of moisture in a soil medium.

There are presently in existence a variety of probes and detectors for use in the detection of moisture present in a medium such as soil. The prior art probes have been found to be inaccurate due to affectation by a variety of soil parameters such as pH variation, and soil salts.

Among the prior art moisture probes which claim reasonable accuracy there are those which utilise electrolysis to determine the presence of moisture and those which measure the surface tension of the medium in which the moisture is present.

Those probes which utilise electrolysis in order to measure soil moisture content can be seriously affected by change in ionic concentrations and soil salts as electrical conductivity during electrolysis is affected by ionic variation. The variations in ion concentrations cause pre-measurement calibrations to be inaccurate making it difficult to accurately measure moisture content in a particular soil.

These electrolysis probes depend for obtaining readings on electrodes which are placed in the soil. The electrodes are linked to electrical circuitry. The circuit is completed by the presence of moisture in the soil enabling an electrolytic ion transfer to take place. This method for measuring moisture content is inaccurate especially when the moisture content of the soil is low. In addition, variation in acidity or alkalinity of the soil increases or decreases conductivity depending upon which of these phenomena occur. As the readings for moisture content are conductivity dependent, variations in conductivity due to these effects introduce significant error into the moisture content readings.

Moisture probes which rely on measurement of surface tension in soil mediums are generally inaccurate.

Many versions of prior art moisture probes are suitable only as indicators of moisture content. Accuracy is sacrificed because of the effects of the medium variables and due to the inherent deficiencies in the prior art probe mechanisms.

SUMMARY OF THE INVENTION

The present invention seeks to provide an accurate moisture detection and measuring probe by adopting a sensing assembly which measures moisture content in a medium such as soil by measurement of the rate of heat loss in a preheated conductor for example in the form of a cap with the rate of heat dissipation in the heated cap being commensurate with the moisture level in the soil medium.

One major advantage of the probe of the present invention is its ability to accurately measure soil moisture content independently of the inhibiting effects of soil parameters such as alkalinity and acidity which parameters can effect moisture readings when adopting prior art methods and apparatuses.

Whilst the probe of the present invention is effective in accurately measuring soil moisture when placed directly into the soil medium to be measured, it has been found by experiment that its performance is enhanced by introducing between the probe and the medium a control environment which eliminates the need for pre-test calibration of the probe before moisture readings are taken. Due to certain constants which are introduced into the testing by use of the control environment the probe is notionally pre-calibrated thereby reducing the possibility of measurement error.

In one broad form the present invention comprises:

A probe for measuring the level of moisture within a medium and from within the said medium;

said probe comprising:

a primary housing, a temperature sensing device located adjacent to, in or on the primary or a secondary housing located at or near one end of said probe and near or adjacent said primary housing, a power cable for delivering a current from a power source to a heating means located in or near said primary or secondary housing, a means for enabling the measurement of the rate of loss of heat generated in said primary or secondary housing by said heating means utilising said temperature sensing device when power from said power source is delivered to thence isolated from said sensing device, said rate of loss of heat being commensurate with the level of moisture in said medium thereby enabling measurement of the moisture level within the medium at a given time.

In an alternative form the present invention comprises:

an assembly for measuring the concentration of moisture within a medium;

said assembly comprising:

a probe having a temperature sensing and a heating means located within or near a housing at the extremity of said probe, a relay circuit interconnected with said probe by a cable means, a power source for providing power to said heating means via said relay, a means to enable the measurement of the rate of heat loss in said housing by utilisation of the temperature sensor when said heating element is deprived of power from said power source, wherein, when the moisture content of a medium is to be measured, said power source is switched off depriving said heating element of power thereby enabling measurement of the rate of heat less in said housing via said temperature sensor.

In another form the present invention comprises:

an apparatus for measuring the concentration of moisture within a medium said apparatus comprising:

an elongated probe, a cable to link a temperature sensor with a power source via a heating element;

a conductive housing at one end of the probe having therein the heating element and the temperature sensor linked thereto, a means for enabling the measurement of the rate of heat loss from said housing when said heating element is deprived of power from said power source, wherein, when the moisture content of a medium is to be measured, said probe is placed within said medium, the heat loss in said conductive housing being measured by said temperature sensor when said heating element is deprived of said power.

In another form the invention comprises a method for measuring the moisture content in a soil medium using a temperature sensing probe: said method comprising the steps of:

a. introducing the probe into a medium in which moisture content is to be measured, b. providing power from a power source to a heating element located near or within a conductive housing on said probe, c. allowing the heating element to heat said heating element thereby heating said conductive housing, d. depriving the heating element of power, e. allowing the conductive housing to cool, f. measuring the rate of heat loss in said housing via said temperature sensor as heat is withdrawn from said housing at a rate proportional to the degree of moisture in said medium.

In another form the invention comprises: a probe for measuring the level of moisture within a medium and from within said medium:

said probe comprising:

a housing of thermally conductive material, a heating means located within said housing for direct or indirect heating of said housing in response to energisation from an energisation means, a temperature sensing means located within and directly or indirectly connected to said housing, said temperature sensing means being adapted to sense temperature changes in said housing when heat is extracted from said housing by contact with said medium.

In the broadest form of the apparatus aspect the invention comprises: a probe for measuring the level of moisture within a medium, by direct or indirect contact with the medium, said probe comprising: means at the leading end of said probe to enable measurement of the moisture level in the medium, said means comprising:

a thermal conductor linked to a heating source, a means for delivering energy from a power source to heat said thermal conductor via said heating source, wherein when said heating means is isolated from said energy source, heat generated in the thermal conductor dissipates, with the heat dissipation rate being commensurate with the level of moisture in said medium thereby enabling measurement of the moisture level within the medium at a given time.

In the preferred embodiment the moisture probe comprises a cable disposed in a metal sheath and which terminates in a conductive housing and provides power to and from the heating element and temperature sensor.

The temperature sensor is located within the conductive metal housing and detects the cooling rate of the housing in response to contact with moisture in the medium.

The temperature sensor is linked via a wire to a relay which is in turn interphased into a computer. The heating of the element is controlled by computer as is the measurement of the rate of cooling of the conductor when the power is turned off.

In another preferred embodiment the probe is adapted with a fixed or detachable environment comprising a vessel having therewithin a medium of substantially constant physical properties into which the probe is inserted to create a notionally calibrated environment.

BRIEF DESCRIPTION OF THE DRAWING

The invention will now be described in more detail according to a preferred but non-limiting embodiment and with reference to the accompanying drawings wherein FIGS. 1a and b show longitudinal sections of the internal features of the probe.

DETAILED DESCRIPTION OF THE PREFERRED EMBODIMENTS

Figure 1A:
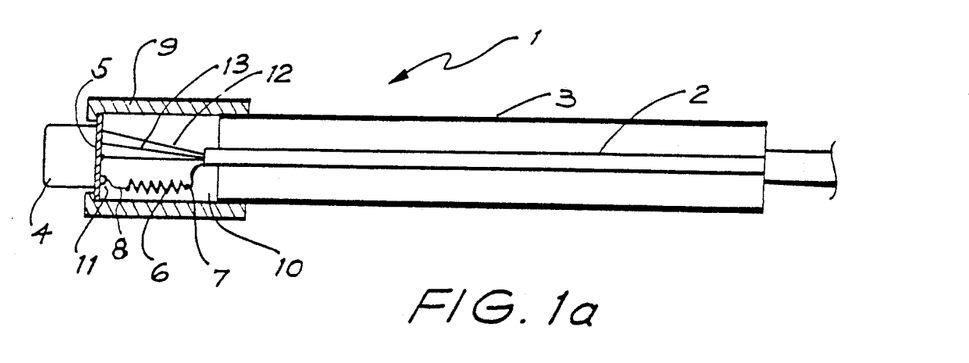
FIG. 1A and 1B are elevational views of a preferred embodiment of the invention according to a preferred embodiment of the invention.
Figure 1B:
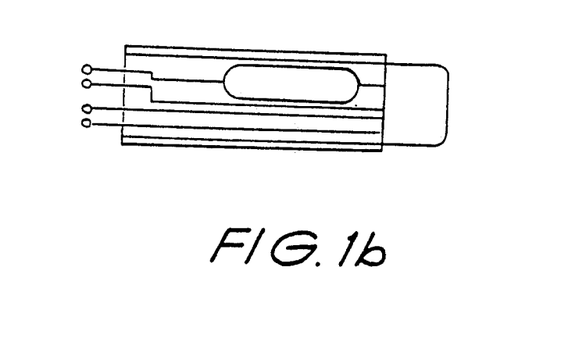

Referring to FIGS. 1a and b there is shown in long sectional views a probe 1 which forms a part of a moisture detection assembly. The assembly also includes a relay of a known kind (not shown) which is connected to a computer (not shown) via a computer interphase.

The computer is adapted with software which controls and receives signals from the probe for conversion into printout data in relation to the moisture content of a soil medium at any given time during the testing period.

The probe 1 according to the preferred embodiment essentially comprises a cable 2 encased within a metal sheath 3. The cable 2 terminates in a conductive housing or cap 4 which houses a temperature sensor 5. The housing 4 also has in indirect or direct contact therewith a heating element 6. The heating element 6 has an AC Power input line 7 and an AC Power output line 8 connected thereto. The housing 4, heating element 6 and temperature sensor 5 are contained within protective sleeve 9 which is moisture proof. Wires 12 and 13 carry analogue data from temperature sensor 5. The heating element 6 and the wires leading to and from the sensor 5 are encased within an epoxy material 10 which spacially separates and electrically insulates the associated wires of the heating element 6 and the temperature sensor 5 from each other. The sensor 5 is preferably a heat sensor of the known variety. The heater is preferably a ¼ watt resistor with approximately ¾ watt of AC Power applied in order to generate the heating. A resistor is suitable for acting as a heater when more power is forced through it beyond its intended design capacity. AC current is used to minimise the build up of scale and corrosion on the conductive housing 4. Other forms of protection of the housing can be employed to increase the life of the housing by preventing unwanted insulation of the housing; for instance the housing 4 can be gold plated.

When in use, power is supplied to the probe and in particular to the heating element (resistor) 6. When the resistor 6 heats up, heat is transferred via metal leg or heat pipe 11 to the housing 4 thereby heating the housing metal. Once the housing 4 is heated by conduction to a predetermined level the power is switched off. The sensor 5 then monitors the rate of cooling of the housing when the power is turned off.

The soil moisture content is measured and is dependant upon the ability of the moisture in the soil surrounding the probe to remove heat from the housing. The rate at which the heat is withdrawn is proportional to the thermal resistance of the soil. The heat withdrawal rate i.e. the cooling of the housing 4 is therefore proportional to the degree of moisture content in the soil medium.

When moisture content of a soil is high the cooling rate of the housing decreases. This interrelationship therefore enables accurate measurement of the moisture content of the soil over a set time period for a selected soil.

Prior to the moisture readings being measured the probe is left in the soil to be measured for at least 10 minutes for stabilisation. Allowance is made in the associated computer software for parameters which may vary from soil to soil.

In addition, the probe measures the ambient temperature of the soil at all times to prevent error resulting from the existing soil temperature.

The probe measures the temperature of the housing 4 via the sensors 400 times/sec. The computer into which the probe is interphased switches the heat off approximately every hour.

Any drying of the soil in the area local to the metal conductive housing 4 which could cause error is overcome by the physical action of capillary which replaces any moisture which may have been dried by the probe. This phenomenon occurs until such time as the soil is completely dry.

Figure 2:
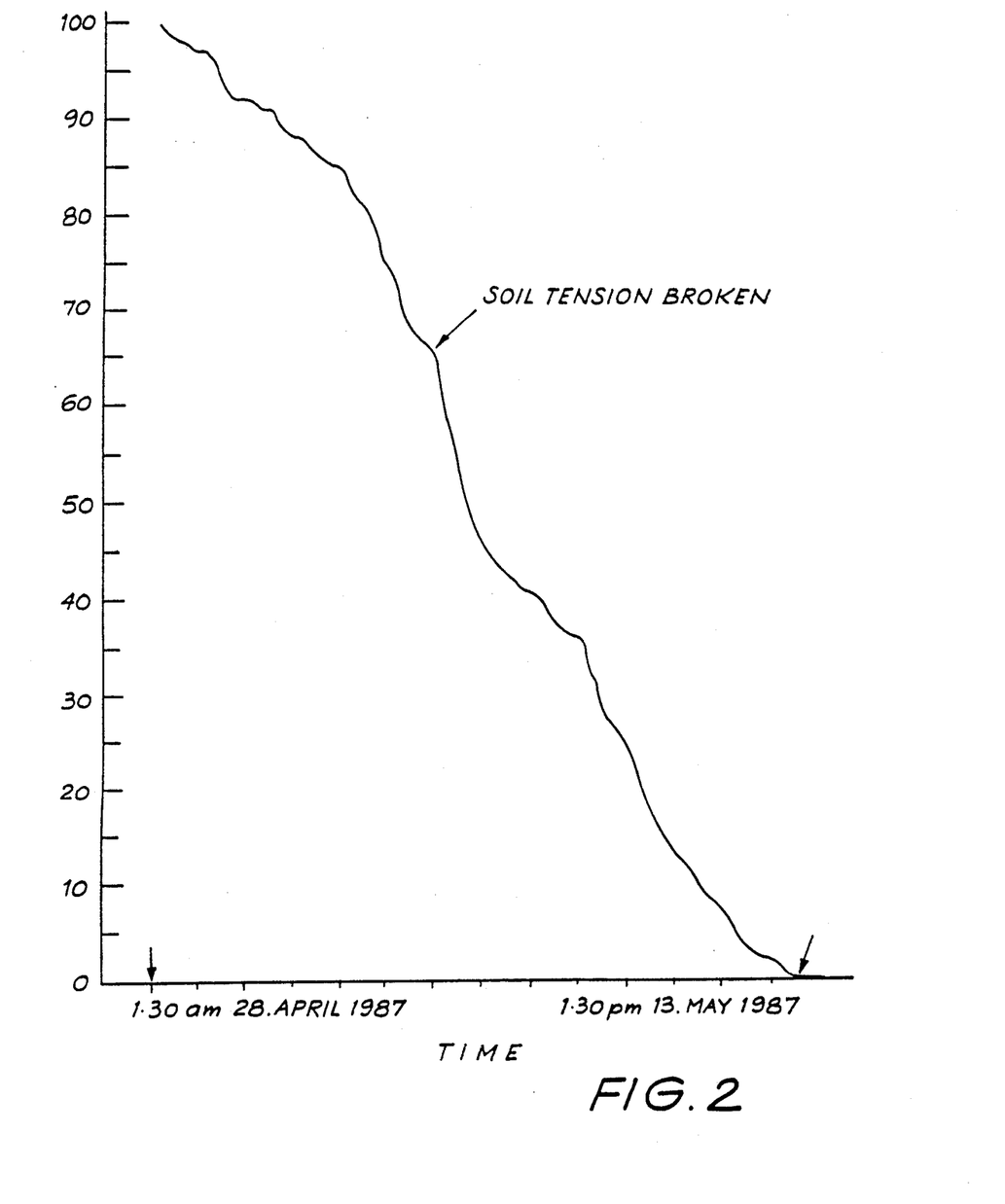
FIG. 2 shows graphical test data on moisture content measurements of coarse quartz river sand over a period of approximately two weeks.
Figure 3:
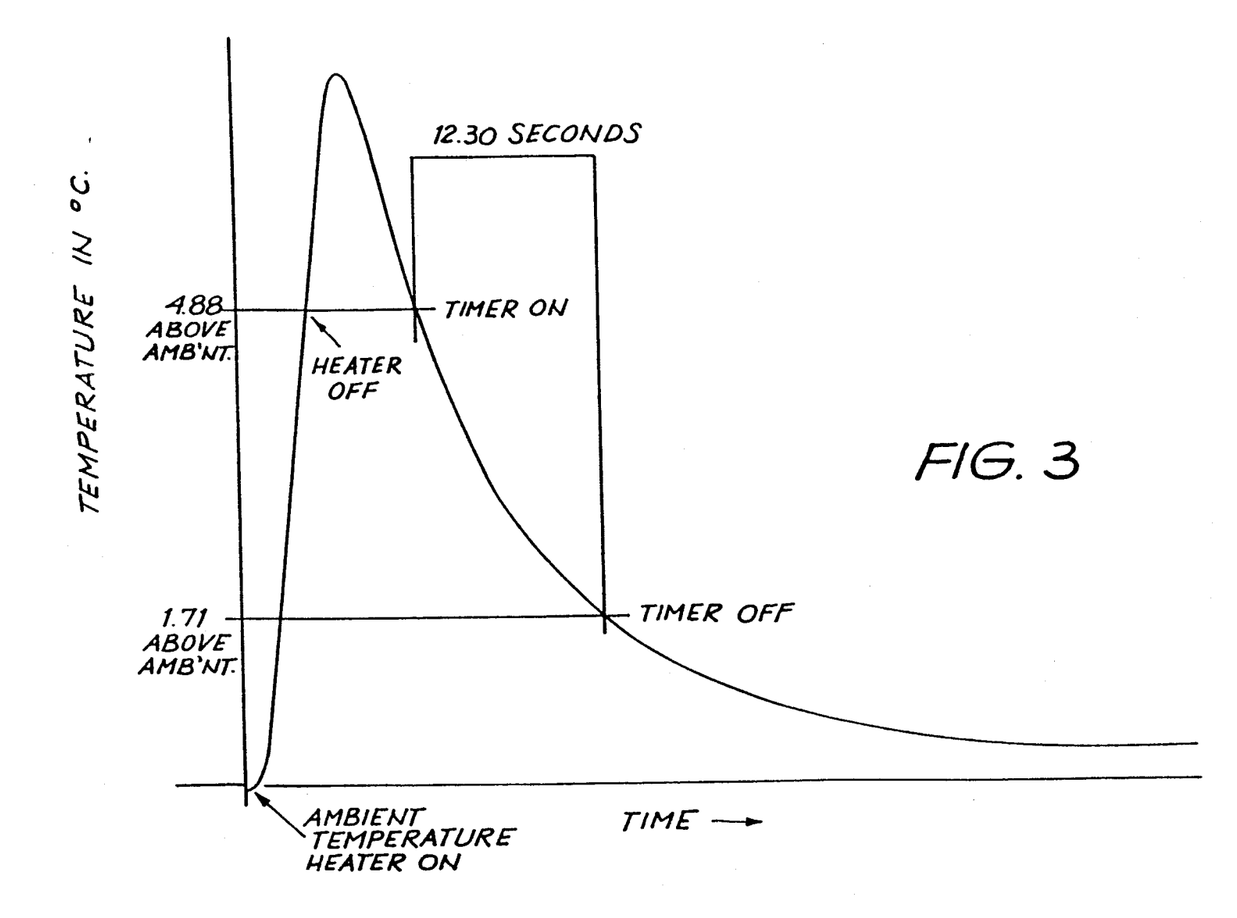
FIGS. 3 to 9 graphically represent a series of test results showing the relationship between percentage moisture content of a soil and rate of cooling of the heated housing.
Figure 4:
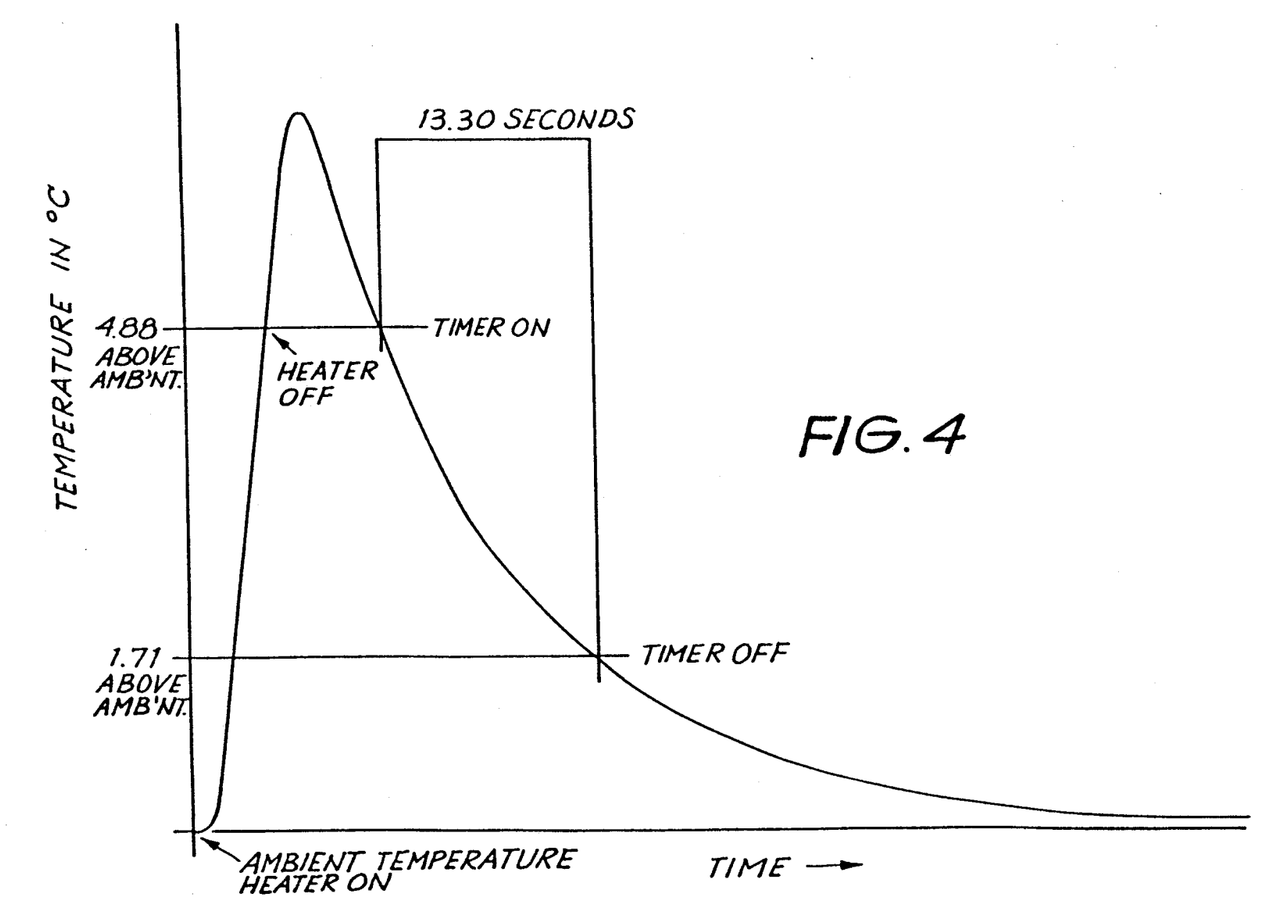
Figure 5:
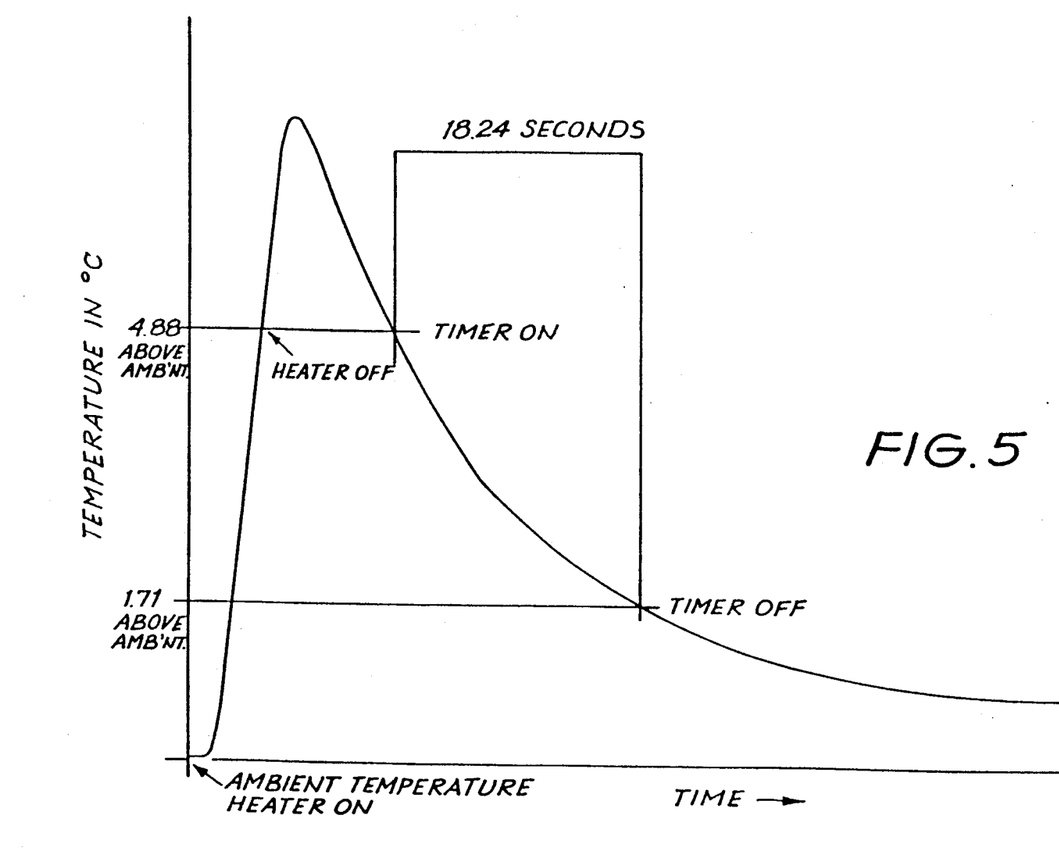
Figure 6:
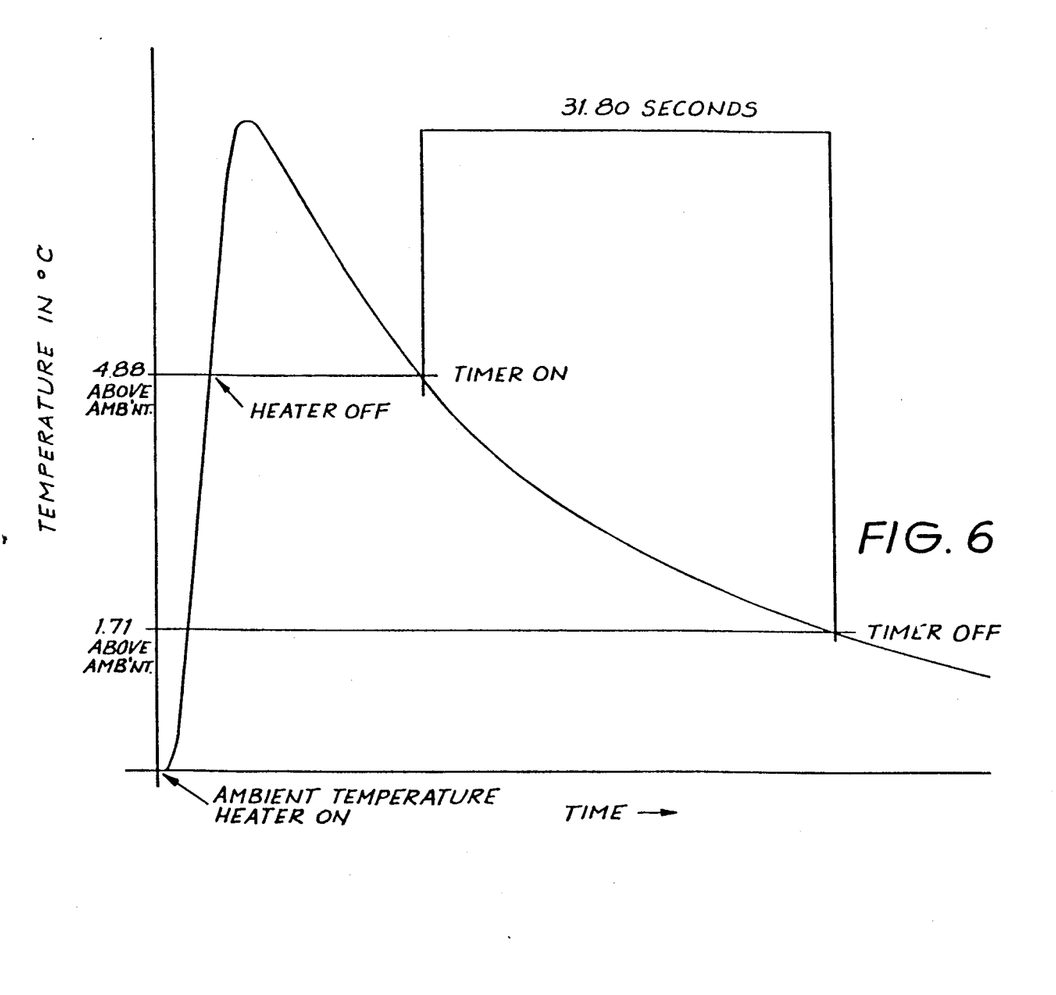
Figure 7:
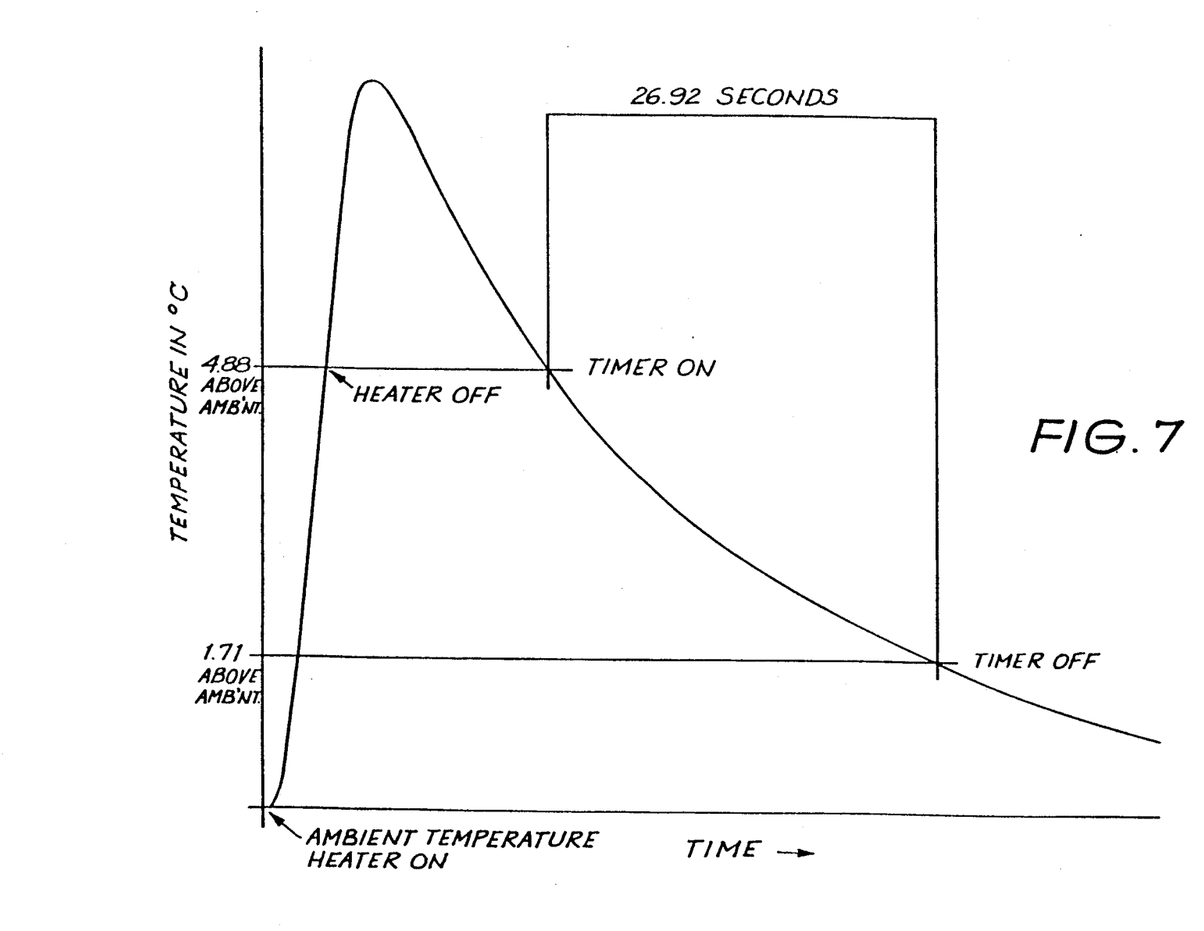
Figure 8:
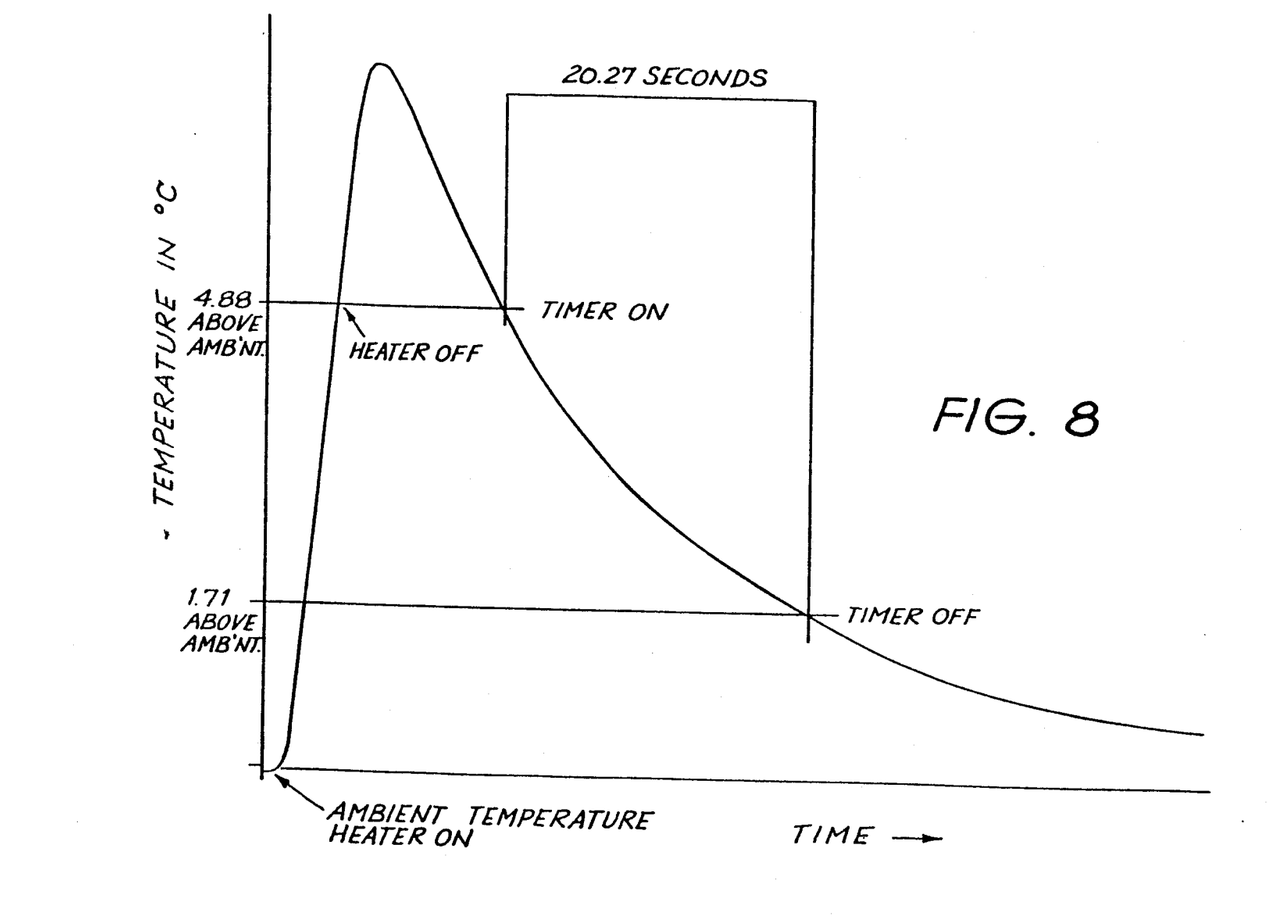
Figure 9:
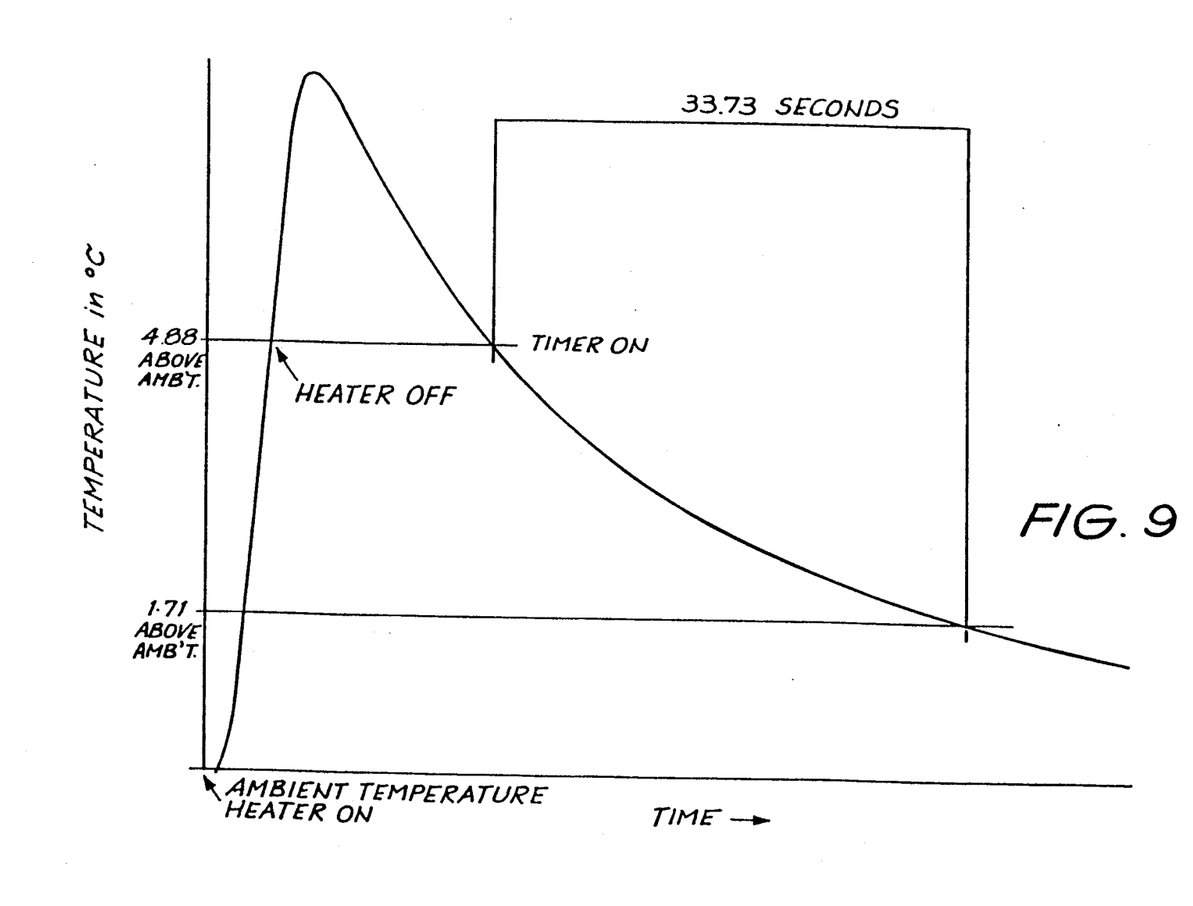

FIG. 2 shows graphical results of a test using the probe conducted over a period of approximately 2 weeks in a coarse quartz river sand soil sample having quick drying properties.

The graph shows the progressive decrease in the moisture content of the soil over the two week period with the accuracy of the results being the the order of 0.1%. The accuracy is due primarily to the method of measurement used which is free from chemical or electrical interference from variable soil parameters.

FIGS. 3 to 9 show a series of graphical test results whereby the moisture probe measures soil moisture at various levels of saturation from 99% to 0%. It can be seen from this graphical data that there is a relationship between moisture content of a soil and the time taken for the housing of the probe, which is heated by the heating element, to cool down after the power to the heating element is switched off.

It can be seen that the heat loss in the conductor of the probe is more rapid when moisture content is higher. It can be seen that the higher the moisture content of the soil being tested for the same temperature range the shorter the time taken to extract heat from the heated housing. At 99% moisture saturation the measured time period for cooling from 4.88° C. above ambient to 1.71° C. above ambient was 12.3 seconds and at 0% saturation the cooling time was 33.73 seconds over the same testing temperature range.

Figure 10:
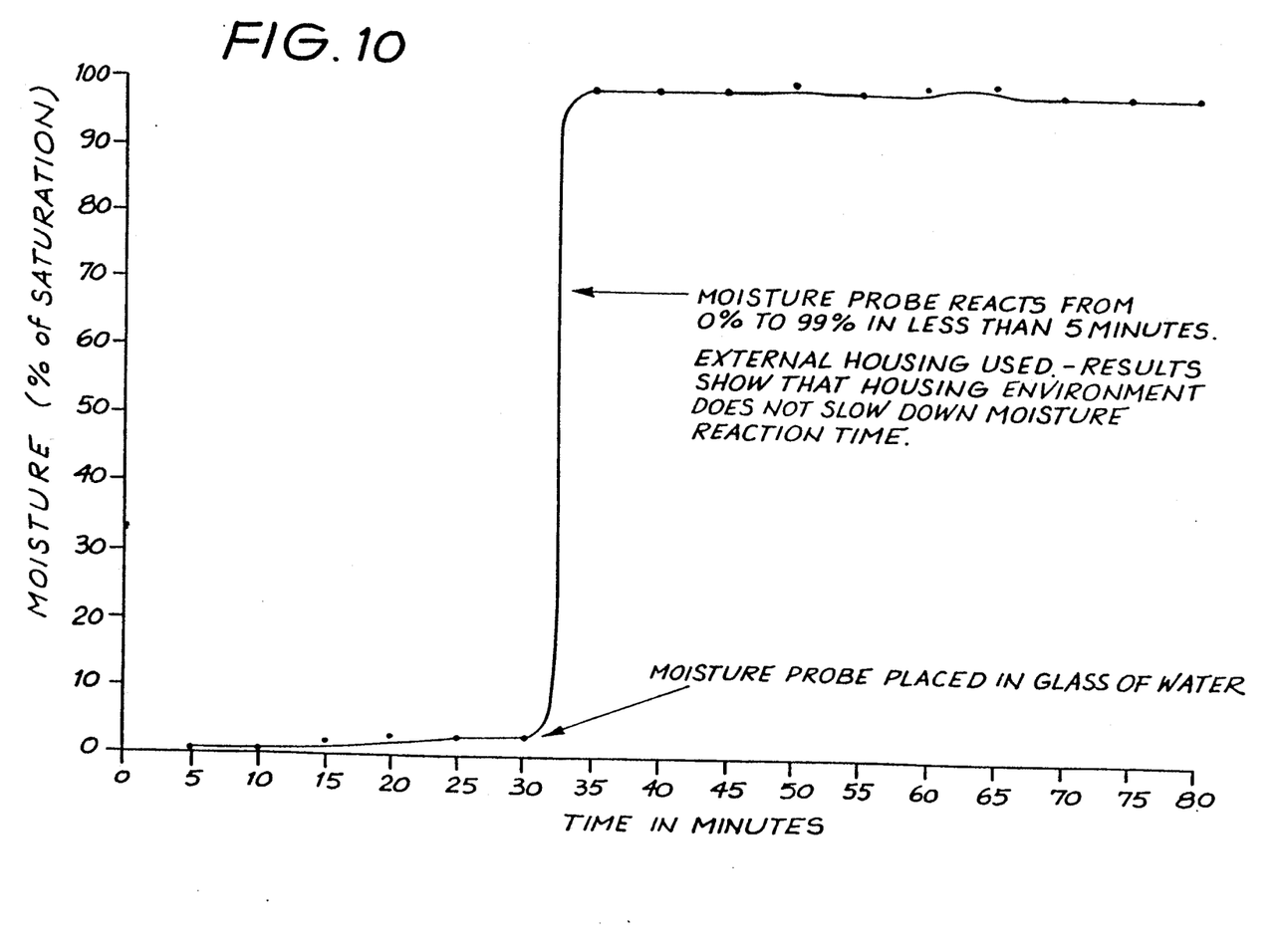
FIG. 10 shows a graph of moisture probe reaction time for moisture contents of 0% to 99%.

FIG. 10 graphically shows moisture probe reaction time for moisture contents of 0% to 99%.

Figure 11:
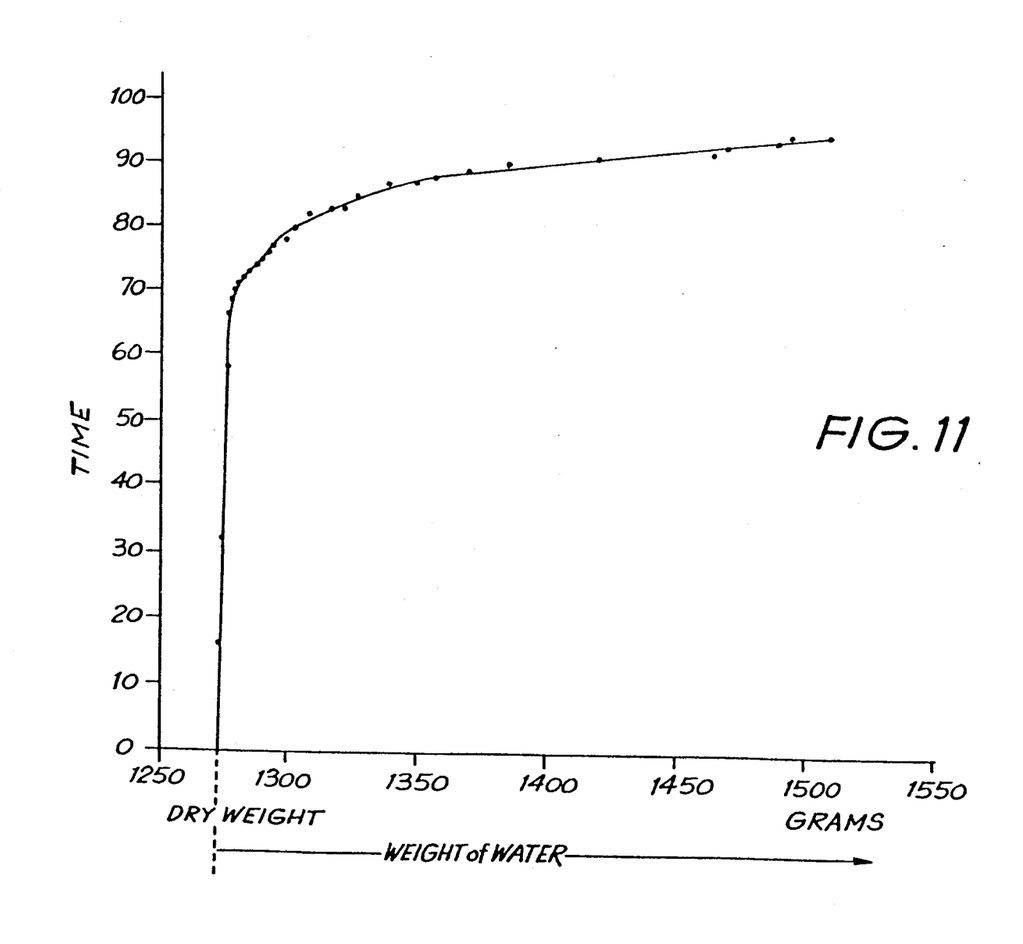
FIG. 11 shows a graphical illustration of a moisture probe calibration test.

FIG. 11 discloses a graphical illustration of a moisture probe calibration test.

In an alternative embodiment, the probe is inserted into a control environment which eliminates the need for calibration of the probe prior to measurement of the moisture content of the medium. The environment preferably comprises a pourex vessel having quartz therein of size 0.5 mm to 0.25 mm. The quartz acts as a buffer zone between the probe and the medium to be measured. The probe when used in this environment is notionally pre-calibrated. The pourex does not prevent water flow but does eliminate many effects created by soil variables.

When the moisture probe is used in the absence of the control environment, on-site calibration of the probe is required to allow for the particular physical conditions of the medium in which moisture content is to be measured. The particular conditions referred to which may necessitate pre-test calibration include particle density, soil tension existence of organic life.

Where the controlled environment is used on-site calibration is required and the following benefits are manifested.

a. The probe needs no on-site calibration.

b. Soil particle density doesn't need classifying.

c. Solid compaction/tension will not affect readings.

d. There is no biologicial interferrence from worms, crickets etc burrowing near the sensor tip.

e. Protection of the thermal electronics/packaging used in the probe.

f. The probe can be used to measure Evapo/transpiration rate.

g. The environment acts as a filter of fine water born particles.

There are numerous uses for the probe of the present invention including the following.

a. Moisture measurement in the sports field/turfgrass industries, and in irrigation control.

b. Breeding drought resistant plants in all agriculture fields.

c. Minimizing water consumption via the irrigation process producing huge saving on water consumption.

d. Grain and food storage monitoring (moisture levels).

e. Mining—deep subsurface water movement though porous rocks.

f. Artesian wall, irrigation control and monitoring.

g. Testing efficiency of soil additives (chemical organic) that either help retain water or assist in water infiltration rates.

h. Monitoring and correcting soil drainage rates.

i. Preventing and calculating irrigations surface run-off rates in irrigation systems.

j. Minimizing erosion of soils.

k. Applied programs can train agriculture plants to develop deeper root systems. Reduction in plant disease, weeks and pests.

l. The probe can also be used in the building industry to monitor and prevent soil swelling/shrinkage caused by soild moisture fluctuations—hence eliminating foundation stress.

m. Monitoring of sub-surface water tables and water table movement in environmental management programs.

n. Monitoring and controlling plant evapo-transpiration processes.

o. Monitoring of moisture density of cloud formations.

p. Prevention of soil salination by monitoring groundwater in specialised irrigation processes.

q. Critical control and help in decision making processes due at harvest time for specialised crops, e.g. Wine industries.

r. Critical control to aid in reclaiming desert and waste lands with absolute minimum water.

One significant advantage that the probe has over the prior art is the accuracy of readings in the lower ranges of moisture. Furthermore the probe is unaffected by changes in soil moisture solinity which affect probes which rely on conductivity. The probe is thus independent of soil conditions other than moisture.

It will be recognised by persons skilled in the art that numerous variations and modifications can be made to the present invention without departing from the overall spirit and scope of the invention as broadly described herein.

The claims defining the invention are as follows.

1. A probe assembly for measuring the level of moisture within a medium, by direct or indirect contact with the medium, said probe assembly including a probe and means to enable said indirect contact between said probe and the medium;

said contact enabling means comprising a vessel having disposed therein a porous medium which acts as a buffer zone, said buffer zone at least partially enveloping said probe; and said probe comprising means at a leading end of said probe to enable measurement of the moisture level, said measurement enabling means comprising:

(i) a thermal conductor linked to a heating source, (ii) a means for delivering energy from a power source to heat said thermal conductor via said heating source, and (iii) a temperature sensor for enabling measurement of the heat dissipation rate in said thermal conductor upon isolation of said heating source;

wherein, when said heating means is isolated from said power source, heat generated in said thermal conductor dissipates, with the heat dissipation rate being measurable by said temperature sensor and commensurate with the level of moisture in the medium, thereby enabling measurement of the moisture level within the medium at a given time.

2. A probe assembly for measuring the level of moisture within a medium, by direct or indirect contact with the medium, comprising:

(A) a probe having apparatus at a leading end thereof to enable measurement of the moisture level, said apparatus comprising:

(i) a thermal conductor via said heating source, and (ii) a means for delivering energy from a power source to heat said thermal conductor via said heating source, wherein, when said heating means is isolated from said power source, heat generated in said thermal conductor dissipates, with the heat dissipation rate being measurable and commensurate with the level of moisture in the medium, thereby enabling measurement of the moisture level within the medium at a given time; and (B) detachable means to create a controlled environment immediately external of said probe so that said probe is in indirect contact with the medium.

3. A probe according to claim 2 further comprising a temperature sensor for enabling measurement of the heat dissipation rate in the thermal conductor, upon isolation of said heating source.

4. A probe according to claims 1 or 3 wherein when measurement of moisture in a medium takes place when the probe is placed within the medium and in either direct or indirect contact with the medium.

5. A probe according to claim 4 wherein the means for delivering energy to the heating source comprises a power cable emanating from an electrical power source.

6. A probe according to claim 5 wherein the thermal conductor comprises a metallic cap.

7. A probe according to claim 6 wherein the heating source comprises an electrical heating element.

8. A probe according to claim 7 wherein at least the temperature sensor and heating element are encased within a housing.

9. A probe according to claim 8 wherein the metallic cap is in thermal contact with the housing.

10. A probe according to claim 9 wherein the metallic cap and the housing are in axial alignment.

11. A probe according to claim 10 wherein the heating means in addition to the heating element also comprises a heat pipe.

12. A probe according to claim 11 wherein the heating element is electrically isolated from the said temperature sensor.

13. A probe according to claim 12 wherein the temperature sensor is integral with the metallic cap.

14. A probe according to claim 13 wherein the temperature sensor is adjacent the metallic cap and is electrically linked to a data receiving, recording and processing terminal.

15. A probe according to claim 14 wherein the metallic cap is gold plated.

16. A probe according to claim 15 wherein the said energy is provided by alternating electric current.

17. A probe according to claim 2 wherein the means to enable said indirect contact between the probe and the medium comprises a vessel having disposed therein a porous medium which acts as a buffer zone, said buffer zone at least partially envoloping the said probe.

18. A probe according to claims 1 or 17 wherein the vessel comprises a base and walls of porous material which form a well into which the probe is inserted.

19. A method for measuring the moisture content of a medium using a probe; said method comprising the steps of:

a. introducing the probe into indirect contact with the medium by insertion of the probe into a porous vessel having a control medium therein, thereby creating a controlled environment and enabling a notational calibration of the probe relative to the medium, b. providing power from a power source to a conductor adjacent the probe via a heating element,
c. allowing the conductor to become heated to a predetermined level,
d. isolating the heating element from the power supply,
e. allowing the conductor to cool,
f. measuring the rate of heat loss in the conductor, via a heat sensor as the conductor cools.

20. The method of claim 19 including the step of calibrating the probe relative to the medium.

21. A probe assembly for measuring the level of moisture within a medium, by indirect contact with the medium, comprising:
(A) a probe having apparatus at the leading end thereof to enable measurement of the moisture level, said apparatus comprising:
  (i) a thermal conductor linked to a heating source,
  (ii) a temperature sensor for enabling measurement of the heat dissipation rate in said thermal conductor upon isolation of said heating source,
  (iii) means for delivery energy from a power source to heat said thermal conductor via said heating source,
  wherein, when said heating source is isolated from said power source, heat generated in the thermal conductor dissipates, with the heat dissipation rate being measurable and commensurate with the level of moisture in the medium, thereby enabling measurement of the moisture level within the medium at a given time; and
(B) a detachable vessel having means to create a controlled environment immediately external of said apparatus, thereby to place said apparatus in indirect contact with the medium, said detachable vessel having disposed therein a porous medium which acts as a buffer zone, said buffer zone at least partially enveloping said apparatus.

22. A probe assembly according to claim 21 wherein said vessel comprises a base and wall of porous material which form a well into which said apparatus is inserted.

* * * * *